United States Patent [19]

Lanyi et al.

[11] Patent Number: 5,671,928
[45] Date of Patent: Sep. 30, 1997

[54] SEAL FOR CHROMATOGRAPHY COLUMN HAVING RIDGES

[75] Inventors: Colin K. Lanyi, Minchinhampton; Geoff Purdom, Oxon, both of England

[73] Assignee: Millipore Investment Holdings Limited, Wilmington, Del.

[21] Appl. No.: 581,656

[22] Filed: Dec. 29, 1995

[51] Int. Cl.[6] .............................. G01N 30/60; F16J 15/32
[52] U.S. Cl. .................. 277/207 R; 277/212 F; 73/61.53; 210/635
[58] Field of Search ..................... 277/207 R, 212 F

[56] References Cited

U.S. PATENT DOCUMENTS

| | | | |
|---|---|---|---|
| 3,312,376 | 4/1967 | Rooney | 277/207 |
| 3,532,446 | 10/1970 | Herreshoff | 277/207 |
| 4,078,810 | 3/1978 | Arendt | 277/207 R |
| 4,858,516 | 8/1989 | Klein | 277/207 R |
| 4,862,786 | 9/1989 | Boyer et al. | 277/207 R |
| 5,167,809 | 12/1992 | Mann et al. | 210/198.2 |
| 5,167,810 | 12/1992 | Vassarotti et al. | 210/198.2 |
| 5,213,683 | 5/1993 | Mann | 210/198.2 |
| 5,282,973 | 2/1994 | Mann | 210/656 |
| 5,288,087 | 2/1994 | Bertoldo | 277/212 F |
| 5,366,621 | 11/1994 | Bidell et al. | 210/198.2 |
| 5,378,361 | 1/1995 | Baeckström | 210/198.2 |

FOREIGN PATENT DOCUMENTS

| | | |
|---|---|---|
| 0 476 996 | 3/1992 | European Pat. Off. . |
| 826521 | 1/1960 | United Kingdom . |

*Primary Examiner*—William A. Cuchlinski, Jr.
*Assistant Examiner*—Christina Annick
*Attorney, Agent, or Firm*—Nields & Lemack

[57] ABSTRACT

An annular seal for chromatography columns adapted for radial sealing with an inner cylindrical surface, having a compressive surface disposed on the inner annular edge of the seal, and a sealing surface disposed on the outer annular edge of the seal, whereas the sealing face is substantially planar and has two parallel edges, which sealing face further comprises at least one release ridge disposed on the sealing surface adjacent to each parallel edge, which release ridge aids in ensuring breaking of the seal between the sealing face and the inner cylindrical surface.

4 Claims, 2 Drawing Sheets

SEAL FOR CHROMATOGRAPHY COLUMN HAVING RIDGES

FIELD OF THE INVENTION

The present invention relates to a seal for a chromatography column piston which allows for reliable, repeatable sealing and repositioning.

BACKGROUND OF THE INVENTION

Chromatography columns of various sizes are known for use in laboratories where the separation of a material into its constituents is carried out for analytical purposes, and in factory installations where the separating action is used for preparation of products such as the constituents of human blood.

The development of chromatography columns has aimed at providing ease of operation and various additional benefits which have particular commercial importance. These include: (a) the ability to be sterilized by autoclaving (b) improved sanitation by virtue of design features giving less carryover of product from one batch to the next, (c) the ability to resist solvents which may be used in the material to be separated, (d) conformity to food grade FDA regulations, (e) an improved pressure tolerance, and (f) lower cost.

Previous designs in this area, most notably as disclosed in U.S. Pat. No. 5,366,621, the entire disclosure of which is incorporated herein by reference, were devised to provide chromatography columns in which the tedious operation of winding the piston along the column tube by a lead screw action during packing or unpacking could be avoided, while still giving the degree of fine adjustment of the piston position deriving from a screw thread traversing action. The chromatography column of U.S. Pat. No. 5,366,621, marketed by Amicon, Inc. (Beverly, Mass.) under the trademark VANTAGE, provides a chromatography column including: a column tube; a movable piston within the column tube; an axially slidable piston rod carrying said piston; a releasable friction clamp for releasing said piston rod for rapid axial traversing of the piston and for clamping the piston rod at or near a desired final position; and means for fine adjustment of the position of the friction clamp axially relative to the column tube, for fine positioning of the piston relative to the column tube.

While these chromatography columns are certainly an improvement over the prior art, there is significant room for improvement in several aspects. For example, users have discovered that the piston seals, while sealing quite adequately to the inner cylindrical surface of the column when compressed radially against that surface, tend to stick tenaciously when the radial compression is removed, making repositioning of the piston difficult. Another problem with seals in this art is that it is not always possible to determine whether a complete seal has been made, short of applying more force than necessary to make the seal (resulting in possible damage to the column and hardware), or running the column erroneously believing that a seal has been made, in which case the operating and chromatographic results will give an after-the-fact confirmation of a poor seal. Since chromatography columns as described above are advantageously made of a transparent material such as glass or polycarbonate plastic, the end of the column piston may be placed very close to the top of the chromatography bed to minimize dead space. However, as the column piston is positioned over the bed, it has been difficult for the researcher to accurately and precisely 'sight' the column piston end over the top of the bed. If the dead space over the column is too large, this leads to a decrease in chromatographic efficiency, and to stagnant flow spots near the column wall, which in turn lead to bacterial growth (also leading to a decrease in chromatographic efficiency.) Lastly, currently available seals are deficient because they allow particles of chromatographic media that has stuck to the column wall during packing to become entrapped between the seal surface and the column wall, leading to poor sealing.

SUMMARY OF THE INVENTION

The invention relates to an annular seal for chromatography columns adapted for radial sealing with an inner cylindrical surface, having a compressive surface disposed on the inner annular edge of the seal, and a sealing surface disposed on the outer annular edge of the seal, whereas the sealing face is substantially planar and has two parallel edges, which sealing face further comprises at least one release ridge disposed on the sealing surface adjacent to each parallel edge, which release ridge aids in ensuring breaking of the seal between the sealing face and the inner cylindrical surface. This seal design provides good releasability with good sealing capability, visual assurance that the seal has been made, and reliable positioning of the seal, which provides a minimal dead space over the column bed, leading to increased chromatographic efficiency, and a substantial reduction in bacterial growth.

DETAILED DESCRIPTION OF THE INVENTION

Figure 1:
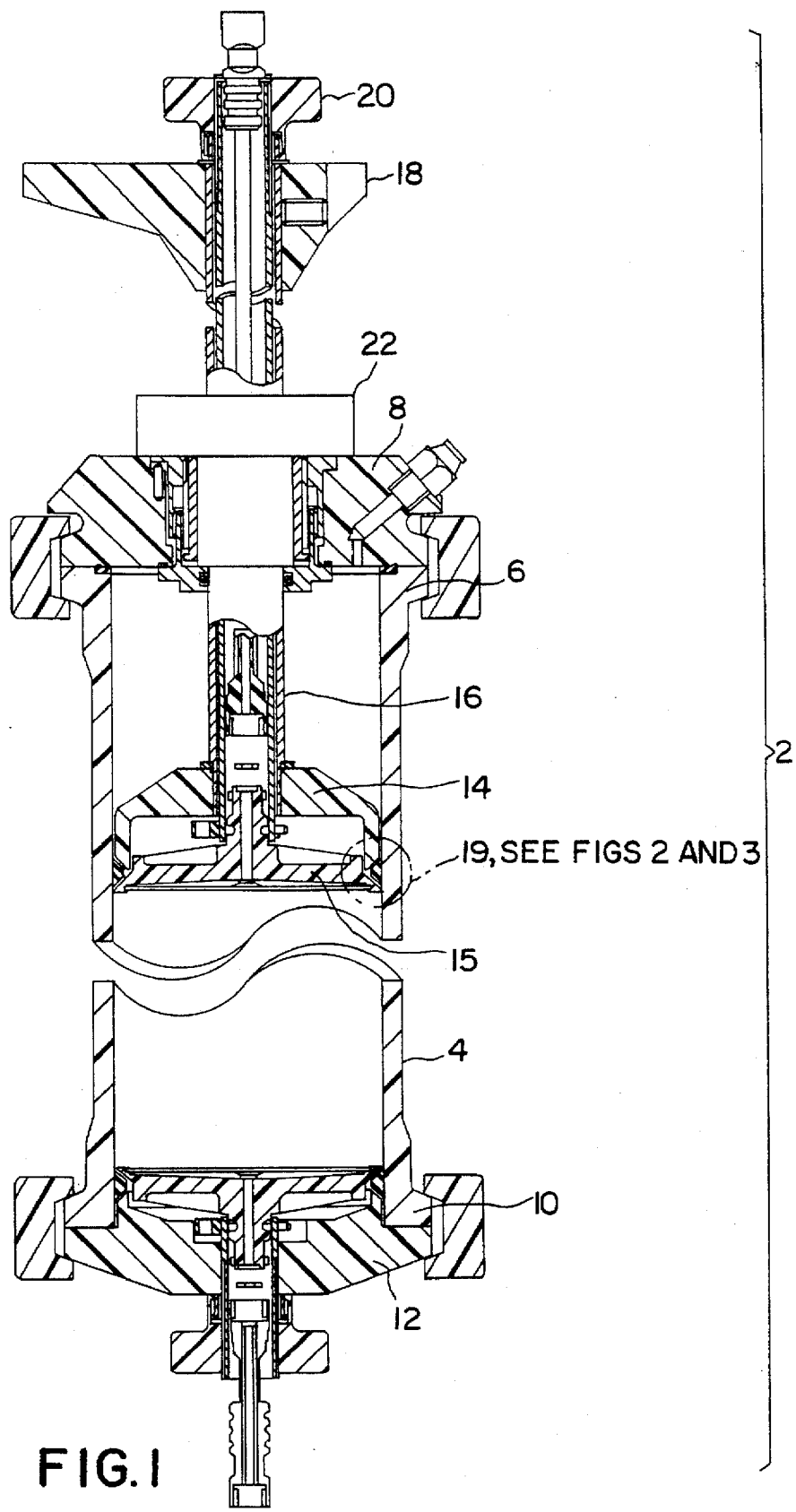
FIG. 1 is a longitudinal sectional view of a chromatography column including the seal of the present invention.

Referring now to the drawings, FIG. 1 shows a chromatography column 2 as disclosed in the aforementioned U.S. Pat. No. 5,366,621. The column comprises a column tube 4 having at its upper end an end flange 6 for clamping to a corresponding flange of an end cap 8, and at its lower end an end flange 10 for clamping to the flange of a bottom end cap 12. Clamping at both ends is by means of a clamp (not shown) which may be a chain clamp or a C-clamp. Traversing along the column tube 4 is a piston 14 on an unthreaded piston rod 16, controlled by a wheel 18 which can be used both to press the piston road axially up and down the column tube 4 and to rotate the piston rod 16, when appropriate. Upper end cap 8 of the column is associated with an adjuster mechanism 22 which can be clamped to provide for threaded fine adjustment of the position of the piston rod 16 or released in order to allow the piston rod to be rapidly traversed up and down the column tube 4, during the re-packing and unpacking operations.

The piston rod also has at its upper end a control wheel 20 for operating the seal on the piston, for example as is described and claimed in European Patent Application No. 9020450.4. Seals of the invention may be specifically adapted for use in such apparatus. Seal 19 is capable of being compressed axially to result in radial expansion to effect a seal against the inner face of the column tube 4. The sealing surface (i.e., the substantially cylindrical radially outer face)

of the seal 19 may be treated to reduce friction, e.g., by coating with polytetrafluoroethylene or by embedding a sheet of polytetrafluoroethylene in the body of the resilient seal material. The resilient seal material may be, for example, an ethylene propylene rubber silicone rubber, butyl rubber, or a thermoplastic rubber, e.g., "Santoprene" (Monsanto Polymer Products Co.). The seal material is self-compensating to the extent that an increase in pressure on the bed below the piston 14 can drive the lower part 15 of the piston upwardly against the upper part in order to increase the axial compression on the seal and hence to thrust the outer face more firmly against the radially inner face of the column tube 4 to ensure that the increased pressure cannot result in gas flow past the seal 19.

Figure 2:
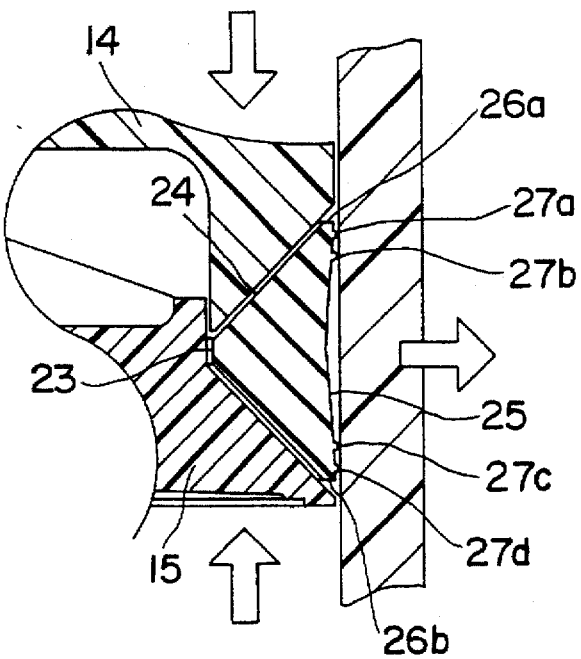
FIG. 2 is an enlarged partial sectional view of the seal in the chromatography column shown in FIG. 1.
Figure 3:
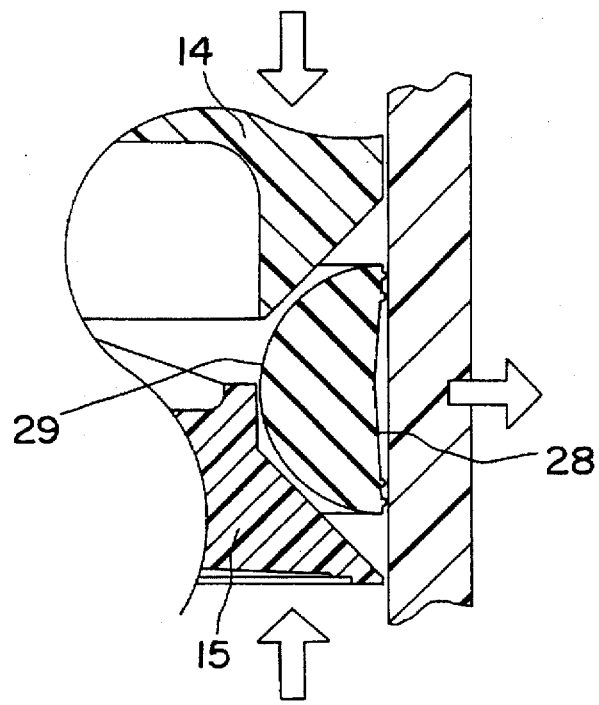
FIG. 3 is a cross-sectional view of another embodiment of a seal shown in a chromatography column in accordance with the present invention.

Seals of the invention are depicted in greater detail in FIGS. 2–3. FIG. 2 depicts, in cross sectional view, a seal 23, with a generally triangular cross-sectional shape, having a compressive surface 24 disposed on the inner annular edge of the seal, a sealing surface 25 disposed on the outer annular edge of the seal, having parallel edges 26a and 26b, and release ridges 27a, 27b, 27c, and 27d formed in sealing surface 25 adjacent to parallel edges 26a and 26b. Release ridges 27a and 27b are spaced apart from and generally parallel to each other, as are ridges 27c and 27d. FIG. 3 shows seal 28, which is similar in design but has a semicircular cross-sectional shape and rounded compressive surface 29. In these drawings two release ridges per parallel edge of the sealing surface are shown, but one ridge per edge may be used, as well as more than two per edge. The location of the release ridge(s) is preferably as close to the parallel edges of the sealing face as possible; this provides a visual aid to the researcher so he/she may "sight" the piston end as close to the top of the column bed as possible to minimize dead space over the column and increase the efficiency of the chromatographic separation.

In operation the sealing surface is radially urged against the inner face of the column tube by applying axial (preferably) or radial pressure to the compressive surface to effect a seal. While a seal may be made with the compression of the release ridges against the inner face of the column tube alone, it may be desirable in some cases to apply additional pressure to the compressive surface to urge a larger area of the sealing surface against inner face of the column tube, i.e., when a stronger seal is desired for operation at higher column back pressures. Whatever the degree of sealing desired, however, the benefit of the release ridges is seen when it is desired to reposition the piston rod, e.g., when the column is repacked. The axial or radial pressure is removed from the seal to 'retract' it from the inner face of the column tube, breaking the seal and allowing repositioning of the piston rod. In the first instance where the seal is made substantially by the release ridges, the potential for the seal to stick to the inner face of the column is minimized because of the small contact area afforded by the release ridges, and the piston rod may easily be repositioned.

However, in the case where additional pressure has been applied to the compressive surface of the seal, the release ridges push the larger area of the sealing surface away from inner face of the column tube, assisting the natural resilience of the seal material, so the seal may be broken easier by axial upward movement of the piston rod.

To attain the desired benefit of ensuring that no particles of chromatographic media sticking to the column wall will interfere with making an effective seal, the piston rod end is positioned at the top of the column. Then, the sealing surface is radially urged against the inner face of the column tube by applying sufficient pressure to the compressive surface to effect compression of the release ridges against the inner face of the column tube, and the bottom of the piston rod end is precisely moved down to the top of the packed bed. More sealing pressure may then be applied if desired (the release ridges provide an instant visual indication through a clear column that a seal has been made.) Two things are accomplished by this method: 1) the release ridges act as a sort of squeegee to clean the inner column wall of particles, ensuring none are trapped between the seal and the column wall, and 2) the dead space is minimized, increasing the chromatographic efficiency.

What is claimed is:

1. An annular seal for chromatography columns adapted for radial sealing with a cylindrical surface, said seal having a sealing face, a first annular edge comprising a compressive surface and a second annular edge spaced from said first annular edge and comprising a sealing surface, said sealing surface being substantially planar and having two parallel edges, said sealing surface further comprising at least one release ridge disposed on said sealing surface adjacent to each parallel edge, which release ridge aids in ensuring breaking of the seal between said sealing surface and said cylindrical surface.

2. The annular seal of claim 1, wherein said sealing surface comprises more than one said release ridge disposed on said sealing surface adjacent to each said parallel edge.

3. A chromatography column comprising a column tube having an inner surface; a moveable piston within said column tube; and means for sealing said piston against said inner surface comprising a seal having a sealing face, a first annular edge comprising a compressive surface and a second annular edge spaced from said first annular edge and comprising a sealing surface, said sealing surface being substantially planar and having two parallel edges, said sealing surface further comprising at least one release ridge disposed on said sealing surface adjacent to each parallel edge, which release ridge aids in ensuring breaking of the seal between said sealing surface and said inner surface.

4. The chromatography column of claim 3, wherein said sealing surface comprises a plurality of release ridges adjacent to each said parallel edge.

* * * * *